(12) United States Patent
Merchant

(10) Patent No.: US 10,973,970 B2
(45) Date of Patent: Apr. 13, 2021

(54) FLUID CONTAINER FOR A HEMODIALYSIS SYSTEM

(71) Applicant: FRESENIUS MEDICAL CARE HOLDINGS, INC., Waltham, MA (US)

(72) Inventor: Stephen Merchant, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 372 days.

(21) Appl. No.: 15/854,685

(22) Filed: Dec. 26, 2017

(65) Prior Publication Data

US 2018/0185560 A1 Jul. 5, 2018

Related U.S. Application Data

(60) Provisional application No. 62/440,306, filed on Dec. 29, 2016.

(51) Int. Cl.
*A61M 1/16* (2006.01)

(52) U.S. Cl.
CPC .......... *A61M 1/1666* (2014.02); *A61M 1/167* (2014.02); *A61M 1/1672* (2014.02); *A61M 2202/064* (2013.01); *A61M 2205/125* (2013.01); *A61M 2205/3317* (2013.01); *A61M 2205/3334* (2013.01); *A61M 2205/7545* (2013.01)

(58) Field of Classification Search
CPC .. A61M 1/1666; A61M 1/167; A61M 1/1672; A61M 2202/064; A61M 2205/125; A61M 2205/3317; A61M 2205/3334; A61M 2205/7545
See application file for complete search history.

(56) References Cited

U.S. PATENT DOCUMENTS 5,318,750 A    6/1994   Lascombes
5,326,473 A *   7/1994   Lascombes ......... A61M 1/1656
                                                                              210/295

(Continued)

OTHER PUBLICATIONS

International Search Report and Written Opinion dated Mar. 23, 2018, for PCT/US17/68447 (21 pages).

(Continued)

*Primary Examiner* — Dirk R Bass

(74) *Attorney, Agent, or Firm* — Kacvinsky Daisak Bluni, PLLC

(57) ABSTRACT

A container for forming a solution for use in a hemodialysis device comprises a first portion comprising a powder, a second portion disposed separate from and in fluid communication with the first portion, and a filter disposed between the first portion and the second portion. The container is configured to receive a fluid flow into the first portion to at least partially dissolve the powder thereby forming a solution, such that the solution and at least a portion of the dissolved powder is passable through the filter into the second portion, and further such that any undissolved portion of the powder is not passable through the filter into the second portion. The filter may be configured such that the solution of the fluid and the at least the portion of the dissolved powder is filtered into the second portion of the container is homogenous.

17 Claims, 8 Drawing Sheets

(56) References Cited

U.S. PATENT DOCUMENTS

| | | | |
|---|---|---|---|
| 5,702,606 A * | 12/1997 | Peter, Jr. | A61L 2/04 |
| | | | 210/646 |
| 6,605,214 B1 | 8/2003 | Taylor | |
| 7,077,956 B2 | 7/2006 | Rovatti | |
| 9,470,341 B2 | 10/2016 | Brehm et al. | |
| 10,493,192 B2 * | 12/2019 | Lura | A61M 1/1668 |
| 10,561,779 B2 * | 2/2020 | Lura | A61M 1/1666 |
| 2004/0217057 A1 | 11/2004 | Rovatti | |
| 2006/0186035 A1 | 8/2006 | Tryggvason et al. | |
| 2011/0120946 A1 * | 5/2011 | Levin | A61M 1/1658 |
| | | | 210/637 |
| 2015/0029817 A1 * | 1/2015 | Orszullok | B01F 15/0085 |
| | | | 366/336 |
| 2017/0239410 A1 | 8/2017 | Lura et al. | |

OTHER PUBLICATIONS

International Preliminary Report on Patentability for International application No. PCT/US2017/068447, dated Jul. 2, 2019, 13 pages.
"Bibag® 2008T Hemodialysis Machine bibag System Operator's Instructions—Quick Reference Guide", Fresenius Medical Care (2013) 4 pages.
Fisher, B.R., "Fresenius Medical Care 2008T Hemodialysis Machine with bibag™ System Special 510(K) Notification", (Report for 510(k) No. K120017), 6 pages. (2011).

* cited by examiner

FLUID CONTAINER FOR A HEMODIALYSIS SYSTEM

CROSS-REFERENCE TO RELATED APPLICATIONS

This application is a non-provisional application of U.S. Provisional Patent Application Ser. No. 62/440,306, filed Dec. 29, 2016, entitled "Fluid Container for a Hemodialysis System," the entirety of which application is expressly incorporated by reference herein.

FIELD OF THE DISCLOSURE

The disclosure generally relates to a fluid container, and more particularly to a fluid container for a hemodialysis system.

BACKGROUND OF THE INVENTION

In some known hemodialysis devices, bicarbonate solution is provided via a container, known as a Bibag®. The Bibag® contains an amount of bicarbonate powder in a single compartment, which is mixed with water from an external source. The solution is then further mixed with water and acids to form a dialysate solution for use in hemodialysis devices.

The amount of bicarbonate powder is typically equal to or more than what is required to saturate an amount of water and/or dialysate flowed into a bibag. As water enters the bibag, it dissolves the bicarbonate therein to produce a bicarbonate solution. In some implementations, this solution is fully saturated with bicarbonate (with possibly excess undissolved bicarbonate remaining in the bibag). When the saturated solution is at a known temperature, as is maintained by typical hemodialysis machines, the bicarbonate concentration of the solution is known. The hemodialysis device then may draw or otherwise rejoin the solution into the fluid stream at a known flow rate and concentration.

Existing systems require a large quantity of water for each treatment, for example, approximately 150 L, to ensure the desired concentration of dialysate, including bicarbonate in solution, to be achieved. A dialysis patient may require dialysis treatments multiple times per week, e.g., every other day, requiring 150 L of water for each treatment. In environments where external water sources are abundant, this amount of water may be accommodated. However, in environments where water is less accessible, for example, in mobile, rural, and/or developing areas, patients may not be able to receive the needed dialysis treatments due to lack of water. If a system is designed to use significantly less water to mix with bicarbonate powder in existing bibags, the powder may not dissolve in the fluid entirely, resulting in a non-homogenous solution, e.g., a powder/sludge-like buildup in the compartment. Thus, the bicarbonate solution is no longer at a constant, known, concentration, but a variable requiring additional controls of the hemodialysis device.

It is with respect to these and other considerations that the present improvements may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

An exemplary embodiment of a container for forming a solution for use in a hemodialysis device in accordance with the present disclosure may include a first portion comprising a powder and a second portion separate from, e.g., disposed vertically below, and in fluid communication with the first portion, and a filter disposed between the first portion and the second portion. The container may be configured to receive a fluid flow into the first portion to at least partially dissolve the powder thereby forming a solution, such that the solution and at least a portion of a dissolved powder is passable through the filter into the second portion, and further such that any undissolved portion of the powder is not passable through the filter into the second portion.

In various of the foregoing and other embodiments of the present disclosure, the container may include that the solution of the fluid and the at least the portion of the dissolved powder filtered into the second portion of the container is homogenous. A cap may be coupled to the container, the first portion of the container being configured to receive the fluid flow via the cap. An exterior of the container may be formed of a medical-grade plastic material. The cap may be removably attachable to the hemodialysis device. In an attached state the first portion may be positioned vertically above the second portion such that the fluid is flowable from the first portion and passable through the filter into the second portion. At least one of the first portion and the second portion of the container may be angled to promote fluid flow. The container may be made of a flexible material. A baffle may be disposed in the container. The baffle may be disposed in at least one of a lower area and upper area of the second portion of the container. One or more baffles may be disposed along sides of the second portion of the container. The hemodialysis device may include one or more sensors for detecting characteristics of the fluid flow into the container. The filter may be coupled to at least a portion of an inner diameter of the container. An outlet may be coupleable to a lower area of the second portion, such that the solution is flowable via the outlet.

An exemplary embodiment of a hemodialysis system in accordance with the present disclosure may include a hemodialysis device, and a container for forming a solution for use in the hemodialysis device. The container may include a first portion comprising a powder, a second portion disposed separate from, e.g., vertically below, and in fluid communication with the first portion, and a filter disposed between the first portion and the second portion. The container may be configured to receive a fluid flow into the first portion to at least partially dissolve the powder thereby forming a solution, such that the solution and at least a portion of a dissolved powder is passable through the filter into the second portion, and further such that any undissolved portion of the powder is not passable through the filter into the second portion.

In various of the foregoing and other embodiments of the present disclosure, the hemodialysis system may include that the hemodialysis device includes one or more sensors for detecting characteristics of the fluid flow into the container. The hemodialysis device may include one or more sensors for detecting characteristics of a fluid flow of the solution in the second portion of the container. The hemodialysis device may be configured to compare the characteristics of the fluid flow into the container to one or more predetermined values. The hemodialysis device may be configured to infuse the fluid flow based on the compared characteristics, such that the solution of the fluid flow and the powder have a concentration determined by the hemodialysis device. The one or more sensors may detect a conductivity of the fluid flow.

An exemplary embodiment of a method for operating a hemodialysis device in accordance with the present disclosure may include a container for forming a solution for use in the hemodialysis device. The method may include flowing a fluid into a first portion of the container, the first portion containing a powder, and forming a solution including the fluid and dissolving at least a portion of the powder. The method may further include filtering the solution of the fluid and at least the portion of the dissolved powder through a filter disposed between the first portion and a second portion of the container, the second portion being disposed separate from, e.g., vertically below, and in fluid communication with the first portion, and the solution passing through the filter into the second portion of the container. In any one or all embodiments of the present disclosure, the portion of the powder in relation to the fluid flow volume may be such that the dissolved powder in the mixed solution is substantially all or all of the powder.

An exemplary embodiment of a container for forming a solution for use in a hemodialysis device in accordance with the present disclosure may include an inlet area, wherein the container is configured to receive a fluid flow through the inlet area, and an outlet area. The container may further include one or more baffles configured to generate a turbulence of the fluid flow in the container and capable of at least partially dissolving a powder with the fluid flow, such that the solution of the fluid and the dissolved powder is passable to the outlet area.

BRIEF DESCRIPTION OF THE DRAWINGS

By way of example, specific embodiments of the disclosed device will now be described, with reference to the accompanying drawings, in which.

DETAILED DESCRIPTION

Figure 1:
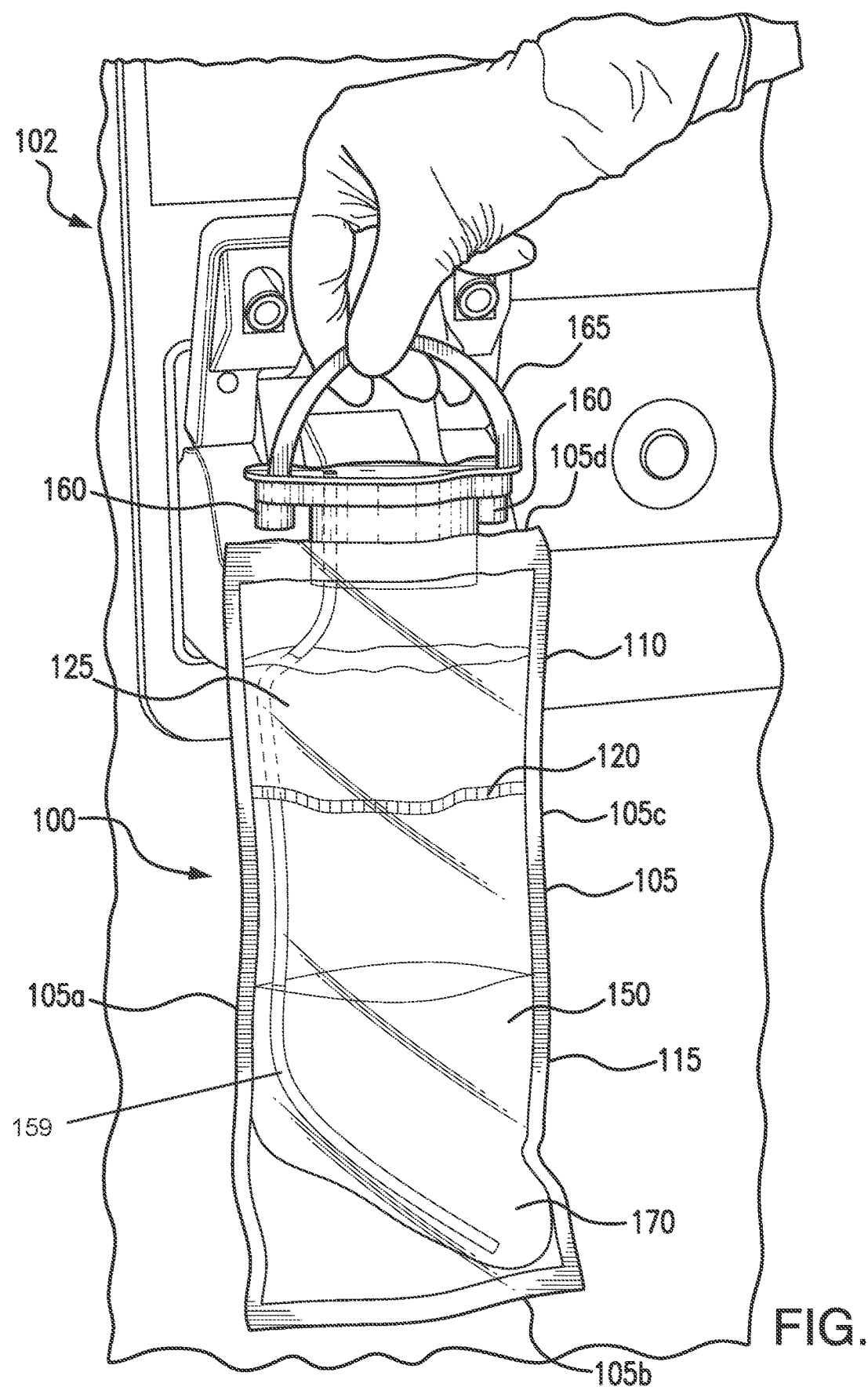
FIG. 1 is a perspective view illustrating an embodiment of a container for a hemodialysis device in accordance with the present disclosure.

The present embodiments will now be described with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Hemodialysis devices require a dialysate composition that includes a bicarbonate component, which is typically provided by mixing a liquid fluid with a powder to generate a bicarbonate solution. The liquid fluid may be water, although hemodialysis devices may also generate fresh dialysate from a spent dialysate. Other components, such as osmotic agents, electrolytes, buffers, or other dialysate components, may be added with the bicarbonate to form the bicarbonate solution, or may be added to form the dialysate composition after the bicarbonate solution is generated. As mentioned, current hemodialysis devices require and are designed to operate with large amounts of fresh water. However, it may be desirable for a hemodialysis system to rely on a limited quantity of fresh water, e.g., 5 L. In mobile, rural, or developing areas where fresh water is not easily obtainable, the hemodialysis device may also be configured to regenerate dialysate from spent dialysate, which is otherwise drained from the system. In an exemplary hemodialysis device requiring 5 L of water for treatment, 1 L may be diverted to generate a bicarbonate solution. To overcome the problems of existing devices, in order to achieve a known bicarbonate concentration of the solution, e.g., 0.75 molar, a known quantity of bicarbonate powder is needed so that the concentration is homogenous. For example, in some systems, 50 g-100 g may be used. In some embodiments, approximately 63 g may be used.

Referring now to FIG. 1, an embodiment of a container 100 for a hemodialysis device 102 is shown. The container 100 may be a flexible bag 105, although other embodiments are envisioned, including a rigid or semi-rigid container, e.g., a hopper, that may be external or internal to the hemodialysis device 102. In some embodiments, at least a portion of the container 100, e.g., an exterior, may be formed of a medical-grade plastic material. The bag 105 may have sides 105a, c, and bottom 105b. The bag 105 may include a first portion 110 and a second portion 115. The first portion 110 may be separate from and in fluid communication with the second portion 115. In some embodiments, the first portion 110 is disposed vertically above the second portion 115 so that a fluid may flow from the first portion into the second portion. The bag 105 may be sealable and waterproof, so that the contents disposed in the bag 105 are contained. For example, the bag 105 may be made of a plastic material, e.g., a medical-grade plastic, and sealed around the sides and the bottom 105a-105c. The bag 105 may be a single-use bag, including a predetermined quantity of powder 125 to be mixed with a quantity of fluid, although some embodiments may include a reusable bag. For example, a preloaded amount of powder 125 may be included in the first portion 110. This is advantageous because single-use, pre-loaded bags ensure a sterilized and contaminant-free environment for hemodialysis treatment.

Figure 6:
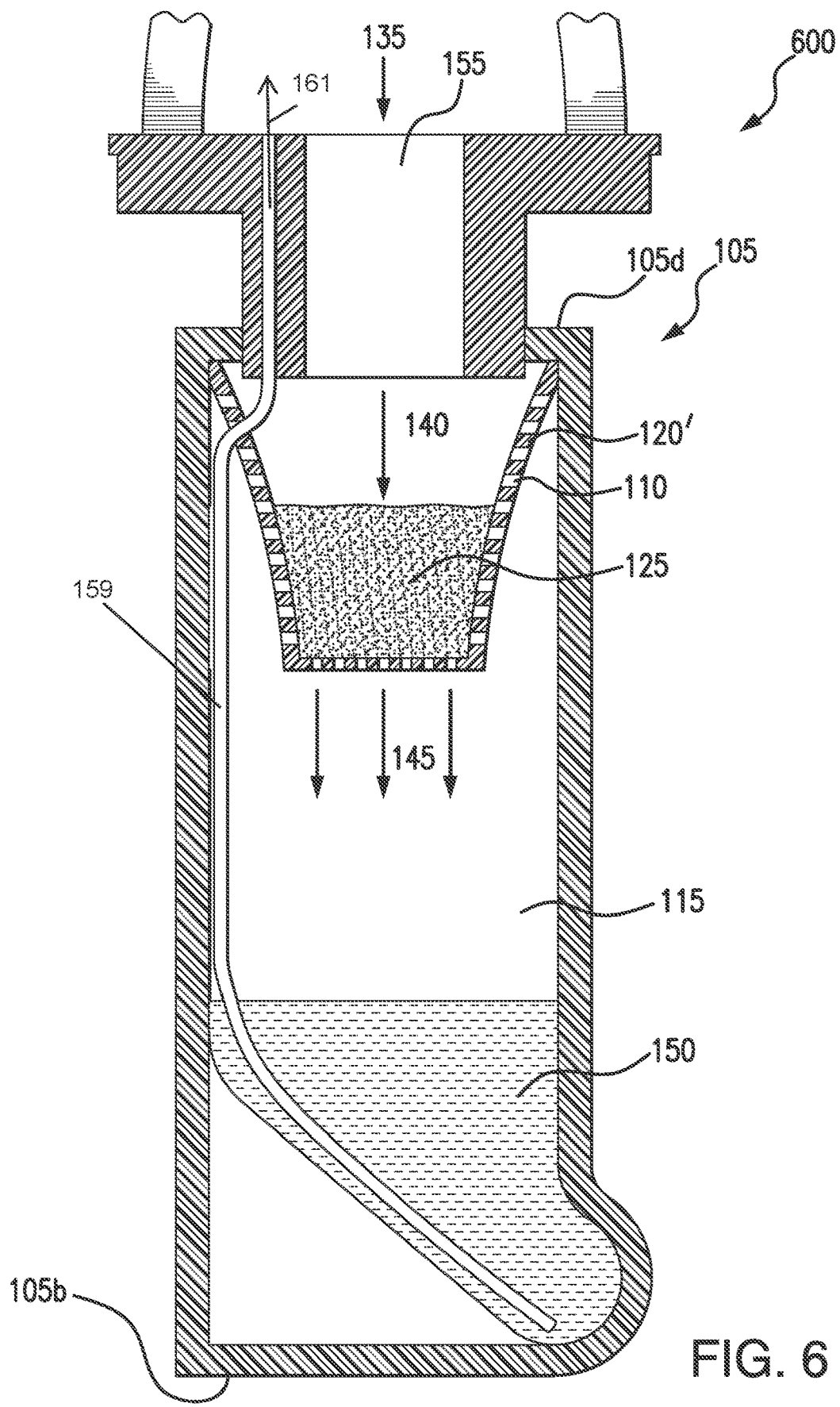
FIG. 6 is a front sectional view illustrating another embodiment of the container for the hemodialysis device in accordance with the present disclosure.

A filter 120 may be disposed between the first portion 110 and the second portion 115 of the container 100, and act as a barrier for the powder 125. The filter 120 may be made of a metal or non-metal material, including but not limited to a wire mesh, paper, cellulose, and the like. In embodiments, the filter 120 may prevent the powder 125 from entering the second portion 115 of the bag 105. In some embodiments, for example, as shown in FIG. 6, a filter 120' may be attached to a top portion 105d of the bag 105, so that the filter 120' forms a first portion 110, separate from second portion 115. In other embodiments, the filter 120 may be entirely enclosed to contain the powder 125 to dissolve when water or other fluid is introduced into the container 100, e.g., similar to a tea or coffee bag filter.

Figure 2:
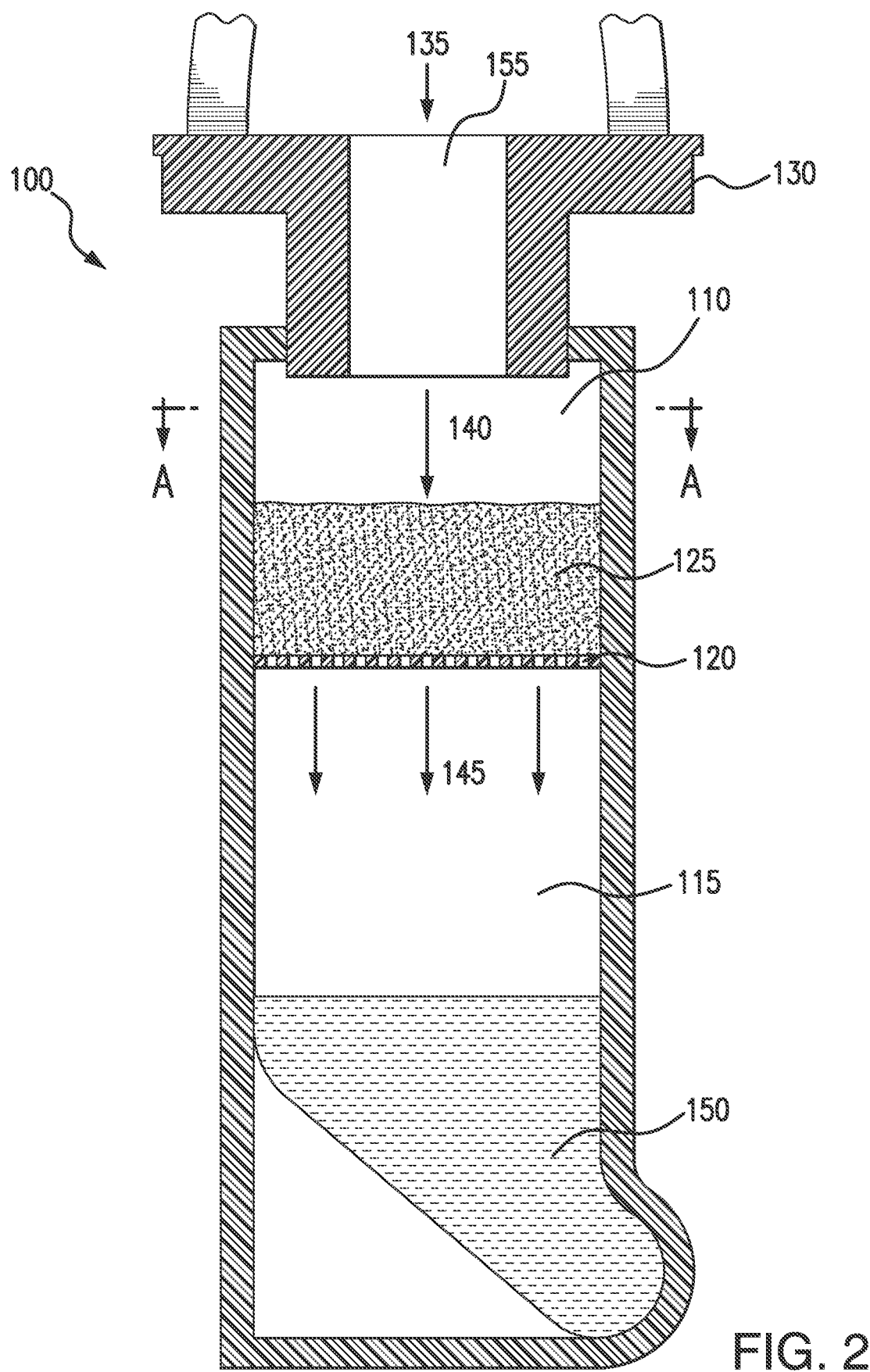
FIG. 2 is a front sectional view illustrating an embodiment of the container for the hemodialysis device shown in FIG. 1.

Referring now to FIG. 2, the bag 105 may receive a liquid fluid from an external source, such as the hemodialysis device 102, entering the container 100 via a cap 130 in the direction marked by arrow 135. The fluid may enter the first portion 110 of the bag 105 in the direction marked as arrow 140. The fluid may mix with the powder 125 and dissolve the powder to form a solution 150 with the components loaded in the powder. As the powder 125 becomes more saturated from the fluid, the mixed solution 150 of the liquid and powder may pass through the filter 120 into the second portion 110 shown by direction arrows 145. The filter 125 may prevent excess powder that has not mixed and/or dissolved in the fluid from entering the second portion 115 of the bag 105, so that any undissolved particles remain in the first portion 110 and the mixed solution 150 is homogenous. The mixed solution 150 of the powder and the fluid in the second portion 115 of the bag 105 may then be used in hemodialysis treatment with the hemodialysis device 102.

The powder 125 may be a bicarbonate powder as described above, although the powder may be any desired concentration of electrolytes, buffers, osmotic agents, and the like for forming or regenerating dialysate. The fluid may be fresh water or may be a spent dialysate, which is a byproduct of hemodialysis treatment. As described in detail below, the mixed solution 150 may be regenerated dialysate for use in hemodialysis treatment.

It is advantageous to provide a container 100 including a first component of the powder 125, while introducing a second component of the fluid from an external source, to form a bicarbonate solution used in hemodialysis, so that the container 100 may be easily transportable and usable, e.g., in geographic locations with limited resources. For example, mobile, rural, and developing areas may have limited access to fresh water. The container 100 according to the present disclosure may include a powder for mixing in low-flow systems with low volumes of fresh water or a spent dialysate that can be regenerated for use. Additionally, by not including the fluid component, but instead providing it externally for immediate mixing, the container 100 may be easily transportable as liquids can increase concerns of leaking, puncture, and weight limits.

Figure 2A:
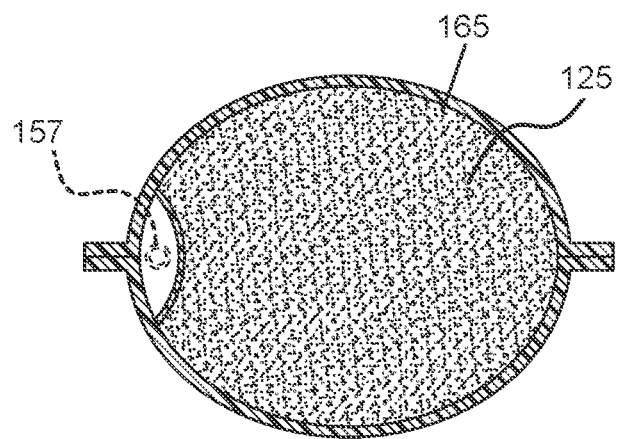
FIG. 2A is a top sectional view illustrating an embodiment of the container for the hemodialysis device.
Figure 2B:
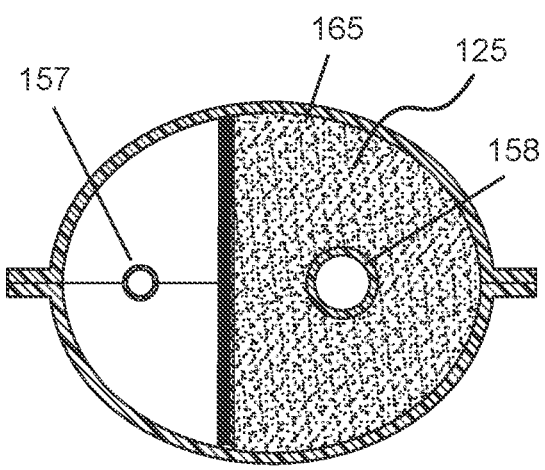
FIG. 2B is a top sectional view illustrating another embodiment of the container for the hemodialysis device in accordance with the present disclosure.

In embodiments, the filter 120 may be coupled to at least a portion of an inner diameter 165 of the bag 105. The filter 120 may be coupled to the inner diameter 165 by adhesives, stitching, and the like. Referring now to FIG. 2A, an embodiment of a top sectional view from A-A in FIG. 2 is shown. The filter 120 may be coupled to the entire inner diameter 165, so that the fluid may only flow into the container 100 via the cap 130, although an outlet 157 may be separate from the filter 120. The solution 150 may flow vertically down into the second portion 115 after passing through the filter 120. Referring now to FIG. 2B, the filter 125 may be coupled to a portion of the inner diameter 165 of the bag 105 so that the outlet 157 is a separate portion from an inlet 158. The outlet 157 may allow for the mixed solution 150 to exit the container 100 in a direction indicated by arrow 161 without interacting with the incoming fluid. It should be understood that the powder 125 and incoming fluid flow through the inlet 158 does not interact with the mixed solution 150 as this may affect the concentration of the bicarbonate solution. The outlet 157 may be coupleable to a lower area 185 of the container so that the mixed solution 150 may be withdrawn from the container. In the illustrated embodiments, a tube 159 may extend from the cap 130 to the lower area 185 of the container so that the mixed solution 150 may be withdrawn through the outlet 157. The tube may extend around and/or through the filter in a manner that retains separate outlet 157 and inlet 158 areas to mitigate mixing between the incoming fluid flow and the outgoing fluid flow.

In other embodiments, a connector (not shown) may be attached to the bottom 170 of the bag 105. The bottom 170 of the bag 105 may be angled to increase fluid flow out of the bag 105. For example, FIG. 1 shows a boot, or toe-shape at the bottom 170 of the bag 105. The connector (not shown), when attached to the bottom 170 of the bag, allows the mixed solution 150 to flow out of the second portion 115 for use in the hemodialysis system 102.

Regardless of the attachment of the filter 120, the cap 130 may be configured to allow fluid flow only as directed through the filter 120 and powder 125, so that the fluid cannot bypass being mixed with the powder 125 and filtering out any undissolved particles via the filter 125 before entering the second portion 115. Such a configuration, for example, may allow the mixed solution in the second portion 115 to exit through the outlet 157 in the cap 130 rather than from a bottom 170 of the bag 105. Various other configurations of the filter covering other portions of the diameter of the bag are contemplated depending upon the dimensions of the bag, depth of filter, flow rate through the filter, filter material, mesh openings, etc.

The cap 130 may be coupled to a top 105d of the bag 105, and include aperture 155 for receiving a liquid fluid from the hemodialysis device 102 to inlet 158. As shown in FIG. 1, the cap 130 may include protrusions 160, to attach to a hemodialysis device 102. The cap 130 may further include a handle 165 to aid a user in attaching the container 100 to the hemodialysis device 102. In some embodiments, gravity may be relied on for the fluid entering the bag via the cap 130 into the first portion 110, which then saturates the powder and passes through the filter 120 to the second portion 115. In some embodiments, as fluid enters the first portion 110 and mixes with the powder, the fluid will flow from an area of higher pressure to an area of lower pressure, e.g., the second portion 115. The solution 150 may flow into the second portion 115 at a predetermined flow rate and flow volume as a function of the fluid flowing into the first portion 110.

Figure 3:
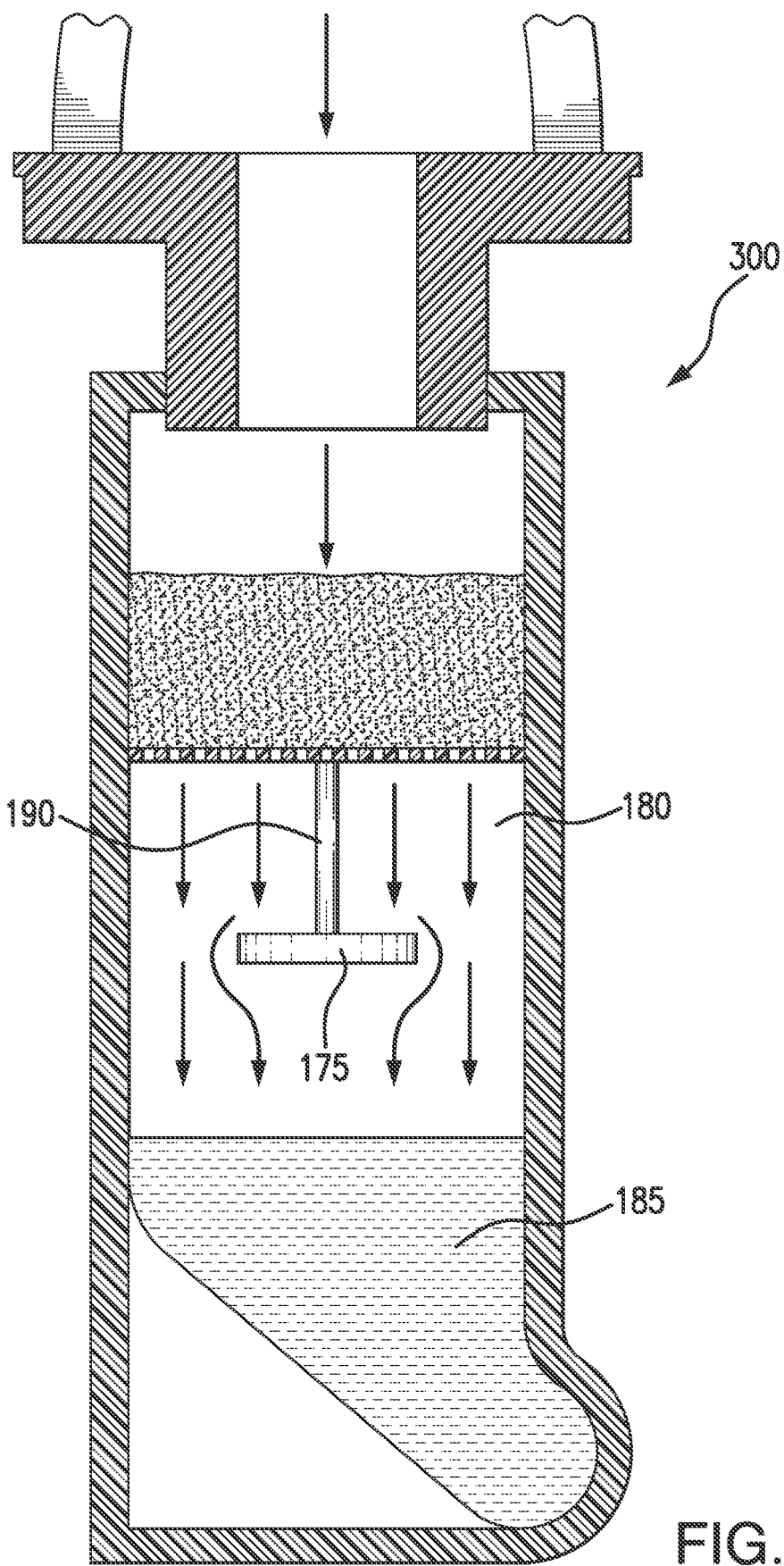
FIG. 3 is a front sectional view illustrating another embodiment of the container for the hemodialysis device in accordance with the present disclosure.
Figure 4:
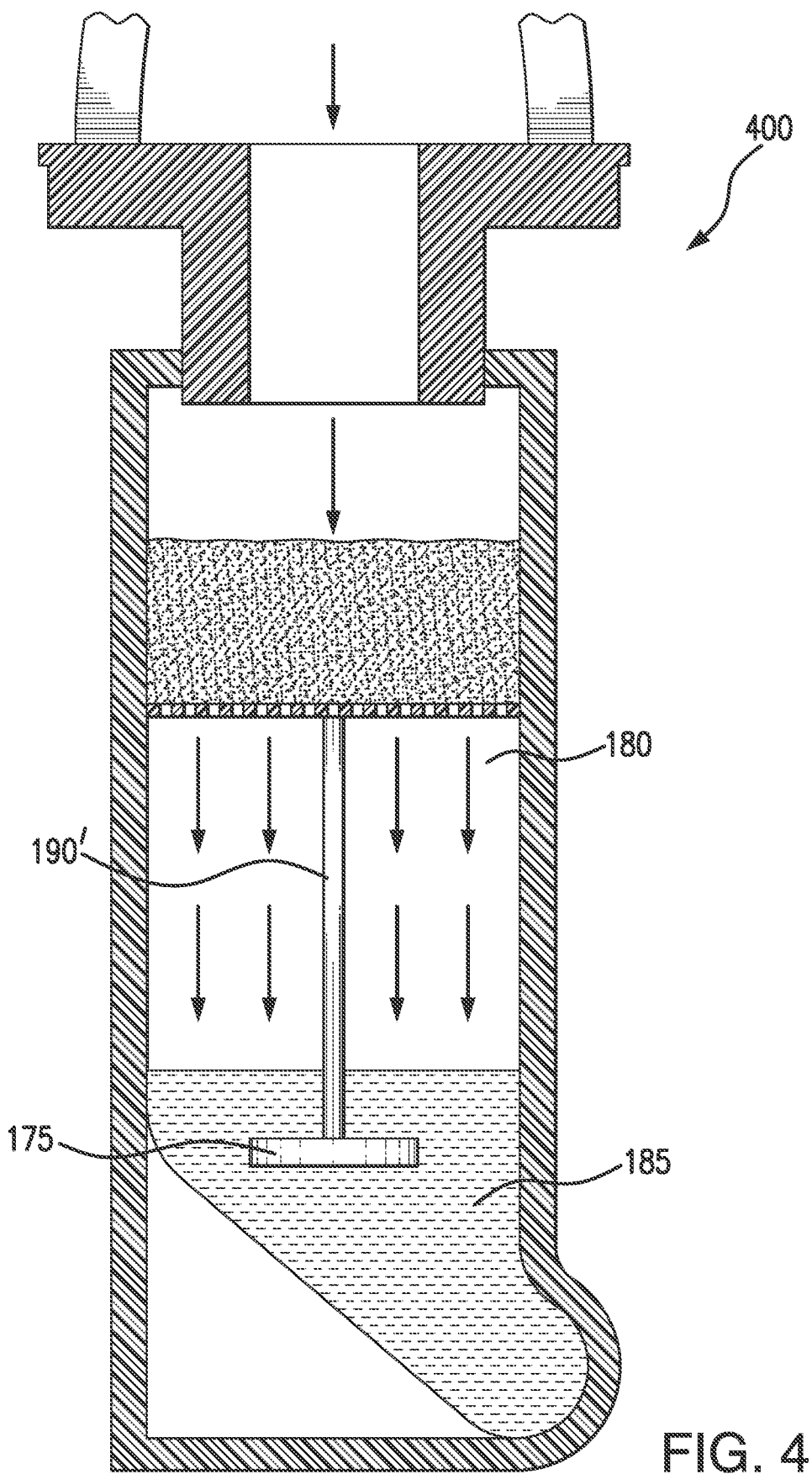
FIG. 4 is a front sectional view illustrating another embodiment of the container for the hemodialysis device in accordance with the present disclosure.
Figure 5:
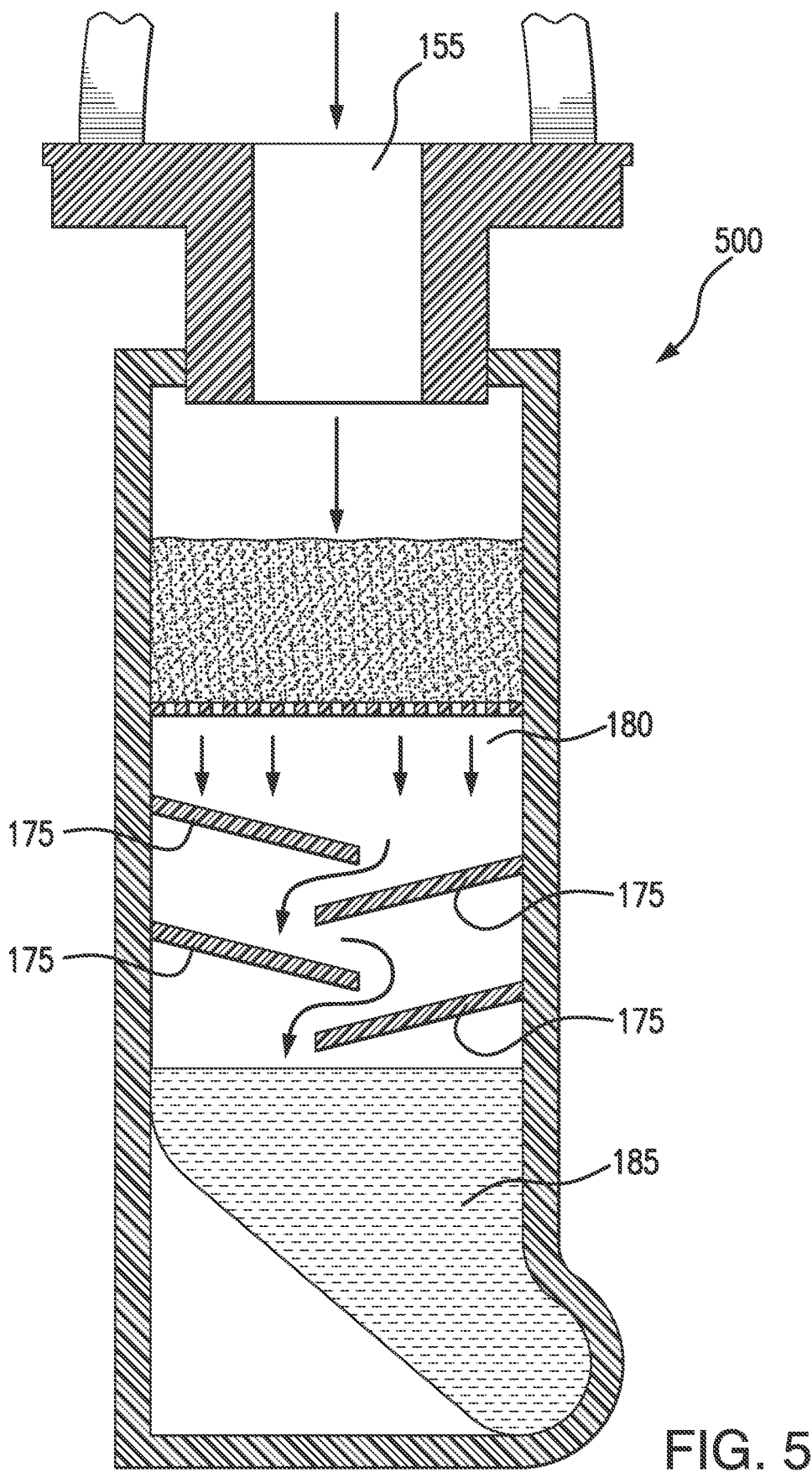
FIG. 5 is a front sectional view illustrating another embodiment of the container for the hemodialysis device in accordance with the present disclosure.

FIGS. 3 to 5 illustrate embodiments of one or more baffles 175 included in the container 100. As illustrated, the baffles 175 may be disposed in the second portion 115 of the bag 105 to aid in generating turbulence of the solution 150 to ensure a homogenous mixture of the fluid and the powder. For example, the baffles 175 may be disc-shaped, although other shapes are envisioned, including but not limited to rectangular, circular, and airfoils. In some embodiments, the baffles 175 may include apertures. According to an embodiment of the present disclosure, a container 100 may include baffles 175 and powder 125 in the same portion. For example, instead of a filter 120 to retain any undissolved powder particles separate from the mixed solution, the baffles 175 may generate turbulence in the mixed solution to achieve homogenization.

The baffles 175 may be disposed anywhere in the second portion 115 of the bag 105 to increase turbulence of the solution 150 after passing through the filter 120. FIG. 3 shows, for example, the baffles 175 positioned towards the filter 120 in an upper area 180 of the second portion 115. FIG. 4 shows the baffles 175 disposed in a lower area 185 of the second portion 115. FIG. 5 shows baffles 175 extending from sides 150a, 150c of the bag 105. The baffles 175 may be attachable in the container 100 by known means. For example, the baffles 175 may be attachable to the first portion 110 and/or filter 120 via an arm 190. The baffles 175 may be attachable to the bag 105 by adhesives and the like. In some examples, the baffles may be configured to rotate or otherwise may move or be moveable in the second portion in order to impart increased turbulence and mixing.

In other embodiments, instead of or in addition to baffles 175 included in the container 100, the container 100 may be configured to receive vibrations, oscillations, or shaking movement to generate turbulence of the mixed solution 150. For example, a motor (not shown) may be connected internal or external to the hemodialysis device so that the vibrations provide the mixed solution 150 with additional turbulence to ensure homogenization. Optionally, a system may be configured for predetermined amounts of powder to be metered into a fluid flow volume from an inventory of powder in the system to provide a mixed homogeneous solution.

For regeneration, the hemodialysis device may include one or more sensors for detecting characteristics of the liquid fluid. For example, when the fluid flow is of a spent dialysate or other dialysate components, the hemodialysis device 102 may analyze one or more characteristic values of the fluid flow, for determining metabolic waste to remove and electrolytes, buffers, and osmotic agents to infuse. The characteristic values may be detected and measured by various sensors, including but not limited to conductivity sensors and optical polarization. The characteristic values may then be compared to one or more reference values that have been predetermined and stored in a memory of the hemodialysis device 102. The compared values then determine what dialysate changes are needed, so that the hemodialysis device 102 may regenerate and/or infuse the dialysate to the proper levels. This system feedback of the characteristics allows for the hemodialysis device to ensure the proper concentration of the dialysate.

Figure 7:
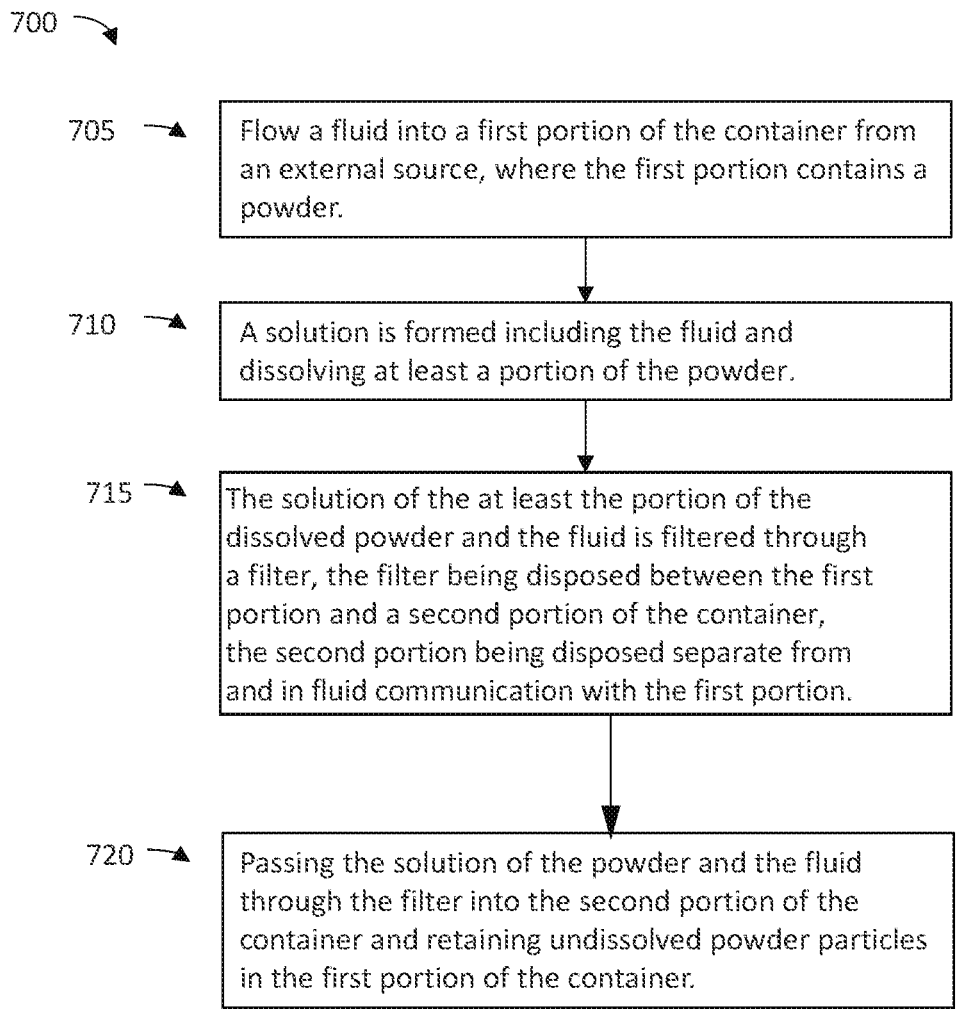
FIG. 7 is a flow diagram illustrating a method of operating a hemodialysis device in accordance with the present disclosure.

Referring now to FIG. 7, a method for operating a hemodialysis device 700 is shown. The hemodialysis device 102 may include a container 100, 300, 400, 500, 600 for forming a solution for use in the hemodialysis device 102. At 705, a fluid may flow into a first portion of the container, where the first portion contains a powder. At 710, a solution is formed that includes the fluid and at least a portion of a dissolved powder. At 715 the solution of the fluid and at least the portion of the dissolved powder is filtered through a filter, the filter being disposed between the first portion and a second portion. In embodiments, the second portion is disposed vertically below the first portion so that gravity aids in the filtering process by allowing the solution to flow downward. At 720, the solution is passed through the filter into the second portion of the container. Any undissolved particles remain in the first portion 110 trapped by the filter, ensuring that the solution 150 in the second portion 115 is homogenous.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A container for forming a solution for use in a hemodialysis device, the container comprising:
    a first portion comprising a powder;
    a second portion separate from and in fluid communication with the first portion;
    a filter disposed between the first portion and the second portion, the filter comprising a first side facing the first portion and a second side facing the second portion;
    a tube extending through the first portion, through or around the first side of the filter and the second side of the filter, and into the second portion;
    wherein the container is configured to receive a fluid flow into the first portion to at least partially dissolve the powder thereby forming a solution, such that the solution and at least a portion of the dissolved powder is passable through the filter into the second portion, and further such that any undissolved portion of the powder is not passable through the filter into the second portion,
    wherein the tube is configured to allow the solution to be withdrawn through the container via an outlet arranged at a top of the bag without interacting with the fluid flow into the first portion.

2. The container according to claim 1, further comprising a cap coupled to the container, the first portion of the container being configured to receive the fluid flow via the cap.

3. The container according to claim 1, wherein in an attached state an entirety of the first portion is positioned vertically above an entirety of the second portion such that the fluid is flowable from the first portion and passable through the filter into the second portion.

4. The container according to claim 1, further comprising at least one baffle disposed in the container, the at least one baffle configured to contact the solution as the solution flows through the container to generate a turbulence of the solution.

5. The container according to claim 4, wherein the at least one baffle is disposed in at least one of a lower area and upper area of the second portion of the container.

6. The container according to claim 1, further comprising one or more baffles disposed along sides of the second portion of the container, the one or more baffles configured to contact the solution as the solution flows through the container to generate a turbulence of the solution.

7. The container according to claim 1, wherein the hemodialysis device includes one or more sensors for detecting characteristics of the fluid flow into the container.

8. The container according to claim 1, wherein the filter is coupled to at least a portion of a side wall of an inner diameter of the container.

9. A hemodialysis system comprising a hemodialysis device and a container for forming a solution for use in the hemodialysis device, the container comprising:
- a first portion comprising a powder;
- a second portion disposed separate from and in fluid communication with the first portion;
- a filter disposed between the first portion and the second portion, the filter comprising a first side facing the first portion and a second side facing the second portion;
- a tube extending through the first portion, through or around the first side of the filter and the second side of the filter, and into the second portion;
- wherein the container is configured to receive a fluid flow into the first portion to at least partially dissolve the powder thereby forming a solution, such that the solution and at least a portion of the dissolved powder is passable through the filter into the second portion, and further such that any undissolved portion of the powder is not passable through the filter into the second portion,
- wherein the tube is configured to allow the solution to be withdrawn through the container via an outlet arranged at a top of the bag without interacting with the fluid flow into the first portion.

10. The hemodialysis system according to claim 9, wherein the hemodialysis device includes one or more sensors for detecting characteristics of the fluid flow into the container.

11. The hemodialysis system according to claim 10, wherein the hemodialysis device includes one or more sensors for detecting characteristics of a fluid flow of the solution in the second portion of the container.

12. The hemodialysis system according to claim 10, wherein the hemodialysis device is configured to compare the characteristics of the fluid flow into the container to one or more predetermined values.

13. The hemodialysis system according to claim 12, wherein the hemodialysis device is configured to infuse the fluid flow based on the compared characteristics, such that the solution of the fluid flow and the powder have a concentration determined by the hemodialysis device.

14. The hemodialysis system according to claim 10, wherein the one or more sensors detect a conductivity of the fluid flow.

15. The container according to claim 1, further comprising a cap coupled to the container comprising an inlet, the first portion of the container being configured to receive the fluid flow via the inlet,
wherein the outlet for withdrawing the solution from the container via the tube is arranged in the cap.

16. The container according to claim 1, the undissolved portion of the powder arranged on the first side of the filter.

17. The container according to claim 1, wherein the filter is coupled to an entirety of a side wall of an inner diameter of the container to divide the container into the first portion and the second portion.

* * * * *